(12) United States Patent
Pullen

(10) Patent No.: US 6,277,389 B1
(45) Date of Patent: *Aug. 21, 2001

(54) NON-TOXIC AQUEOUS PESTICIDE

(76) Inventor: Erroll M. Pullen, 11230 N. Scioto Ave., Tucson, AZ (US) 85737

( * ) Notice: Subject to any disclaimer, the term of this patent is extended or adjusted under 35 U.S.C. 154(b) by 0 days.

This patent is subject to a terminal disclaimer.

(21) Appl. No.: 09/418,058

(22) Filed: Oct. 14, 1999

Related U.S. Application Data

(63) Continuation-in-part of application No. 09/282,963, filed on Mar. 31, 1999.

(51) Int. Cl.⁷ .......................... A61K 31/00; A01N 25/00; A01N 25/32; A01N 61/00
(52) U.S. Cl. ........................... 424/405; 106/17; 424/406; 514/1
(58) Field of Search .................................. 424/405, 406; 106/17; 514/1

(56) References Cited

U.S. PATENT DOCUMENTS

| | | | | |
|---|---|---|---|---|
| 5,110,804 | * | 5/1992 | Lee | 514/60 |
| 5,753,593 | * | 5/1998 | Pullen et al. | 504/150 |

* cited by examiner

*Primary Examiner*—Deborah K. Ware
(74) *Attorney, Agent, or Firm*—Arthur W. Fisher, III

(57) ABSTRACT

A non-toxic aqueous pesticide and method for application on plants and animals comprising at least one surfactant and at least one high terpene containing natural oil to effectively control insects and parasites such as darkling beetles, lice, ticks, mites, flies, aphides, mosquitoes and chiggers.

9 Claims, No Drawings

NON-TOXIC AQUEOUS PESTICIDE

CROSS REFERENCE

This is a continuation-in-part application of a co-pending application Ser. No. 09/282,963 filed Mar. 31, 1999.

BACKGROUND OF THE INVENTION

A non-toxic aqueous pesticide to effectively control insects and parasites such as darkling beetles, lice, ticks, mites, flies, aphides, mosquitoes and chiggers.

FIELD OF THE INVENTION

Various parasites such as lice, ticks, mites, aphides and chiggers attack untreated and unprotected animals and plants. Poultry are particularly susceptible to parasitic infestations, both internal and external. If left uncontrolled, poultry diseases and parasites can result in reduced productivity and high mortality rates. Thus, effective management and sanitation practices, vaccination and medication are essential to prevent and control diseases and pests.

Where poultry is involved, the larvae of these pests attach to the wings and parts of the body injecting a poisonous substance that irritates the skin and causes itching. Such infestation is manifest in lesions observable when birds are dressed. This, of course, reduces the value of the poultry. Moreover, the young birds become droopy, refuse to eat and can die.

In the past, various oils have been used to control insects and mites. Recently, however, renewed attention has focused on the use of oils as a natural substitute for traditional insecticides with attendant toxic and other dangerous side effects.

These oils include horticultural oils which are highly refined petroleum products than can be mixed with water for application for control of target insect and mite pests without deleterious effects. Modern horticultural oils do not include vegetable, fish or whale oils.

Horticultural spray oils are the low toxicity alternative to broad spectrum insecticides. Since the mechanism of insect and mite control with spray oils is by suffocation and/or repellency of egg laying females, there is no requirement for the addition of toxic chemicals. These properties are a valuable and well recognized component of the practice of integrated pest management where oil spraying is intrinsically linked to natural control of pests by predators and parasitoids. Horticultural spray oils are formulated on highly refined clear oil with a minimum of nonionic surfactant. Independent environmental impact studies have shown that D-C-TRON has no detrimental effect on the environment. Mammalian toxicity studies published in the American Journal of Industrial Medicine have shown that oils at this refinement level are non-toxic and non-carcinogenic.

Aqueous suspensions of malathion, stirofos, Ravap and carbaryl formulations (0.25 to 1.0 per cent) have been tested as dips for control of the northern foul mite (NFM), Ornithonyssus sylviarum (Canestrini and Fanzago) on caged White Leghorn hens. Hens treated with Ravap showed symptoms of organophosphorus insecticide poisoning soon after treatment and some died as a result of the dip. However, dipping with the other insecticides did not result in any apparent toxic effects. Malathion was observed to provide residual control of mites for about 4 weeks post-treatment, but both stirofos and carbaryl dips gave complete control for at least 6 weeks against repeated challenges with the NFM. There were no significant differences in the percent hen-day egg production, feed consumption, or body weight of the hens that could be attributed to any of the chemical treatments.

Generally, oil sprays are safe to humans. These oil sprays have little, if any, negative effect on wildlife and non-target insects in the environment. Furthermore, oil sprays are less toxic due to the method by which they kill target pests. In particular, the thin film of oil covers the target insect or mite and plugs the spiracles or pores through which the pests or parasites breathe. The cause of death is primarily suffocation. Large, motile insects and animals that breathe by another method are not affected by these oils.

Another advantage of oil applications is the absence of objectionable odors. In addition, oils are relatively inexpensive and significantly less expensive than many insecticides.

Unfortunately, there are limitations to the use of oil treatments. For example, oils are only effective against those pests that are thoroughly coated by the spray solution. This usually means that only small, immobile or slow moving pests that are exposed on the surface of the poultry, animal or plant at the time of application will be controlled.

Since oil sprays only work by contracting and covering the target pest, thorough application is essential. Missed surface areas provide a safe refuge for the target pests.

U.S. Pat. No. 5,693,344 shows a hazard-free method for controlling insects using a non-toxic composition in the form of a fragrance and crystalline particles which puncture directly through the exoskeleton of an insect. In operation, the particles work themselves between the insect's protective body plates and then puncture the exoskeleton permitting entry of the fragrance into the body of the insect. Once inside, the particles absorb up to four times their weight of the vital body fluids of the insect and the fragrance has a neural effect on the insect.

Thus, there remains a need for a non-toxic pesticide that can be effectively applied to the host to control or kill by contacting the target pests.

SUMMARY OF THE INVENTION

The present invention relates to a non-toxic aqueous pesticide and method for application on plants and animals comprising at least one surfactant and at least one high terpene containing natural oil to effectively control insects and parasites including lice, ticks, mites, aphides and chiggers.

High terpene containing natural oil as used herein means those natural oils having a terpene content of at least 50 per cent. It is preferable that the high terpene natural oil contains at least 90 per cent. Suitable high terpene containing natural oils includes oil from conifers such as citrus peel oils, preferably orange oil, grapefruit oil, lemon oil or pine oil. Of these, orange oil is the most preferred. Naturally, the amount of high terpene containing natural oils in the non-toxic aqueous pesticide will depend upon the amount of terpenes in the specific oil used.

The surfactant may comprise conventional surfactants such as anionic and nonionic surfactants. Preferred are anionic surfactants such as salts of fatty acids, alkyl sulphates, alkyl ether sulphonates and alkyl aryl sulphonates.

The non-toxic aqueous pesticide may also contain various additives such as antioxidants, preservatives, pH neutralizers and/or clarifiers.

Since the non-toxic aqueous pesticide is an aqueous composition, the balance of the non-toxic aqueous pesticide is water.

In use, the non-toxic aqueous pesticide is diluted and sprayed or misted on the host of from about 2 per cent to about 6 per cent solution but preferably about 4 per cent solution, whether plant or animal, to contact the surface of the target pests. In some cases, repeated applications may be required.

When so applied, the non-toxic aqueous pesticide is effective in controlling darkling beetles, lice, ticks, mites, flies, aphides, mosquitoes and chiggers. The mechanism of insect and mite control with spray oils is believed to be by suffocation and/or the dissolving of the waxy layers of the insect's exoskeleton. There is no requirement for the addition of toxic chemicals thereby causing an imbalance in the insect and/or parasites delicate body moisture balance. As such, the instant invention provides a virtually non-toxic alternative to broad spectrum insecticides.

The invention accordingly comprises the features of construction, combination of elements, and arrangement of parts which will be exemplified in the construction hereinafter set forth, and the scope of the invention will be indicated in the claims.

DETAILED DESCRIPTION OF THE PREFERRED EMBODIMENT

The present invention relates to an environmentally compatible non-toxic aqueous pesticide comprising at least one surfactant and at least one high terpene containing natural oil to effectively control target insects and parasites including darkling beetles, lice, ticks, mites, flies, aphides, mosquitoes and chiggers found on plants and animals. The invention also includes the method of application of the non-toxic aqueous pesticide.

High terpene containing natural oil as used herein means those natural oils having a terpene content of at least 50 per cent. It is preferable that the high terpene natural oil contains at least 90 per cent. Suitable high terpene containing natural oils includes oil from conifers such as citrus peel oils, preferably orange oil, grapefruit oil, lemon oil, or pine oil. Of these, orange oil is preferred and cold pressed orange oil the most preferred.

Naturally, the amount of high terpene containing natural oils in the non-toxic aqueous pesticide will depend upon the amount of terpenes in the specific oil used. Generally, the non-toxic pesticide composition contains from about 1 per cent to about 15 per cent by weight of high terpene containing natural oil, preferably from about 4 per cent to about 10 per cent by weight and more preferably from about 5 per cent to about 7 per cent by weight.

While not to be bound by theory, it is believed that the terpenes in the natural oils provide a mechanism for the efficacy of the instant invention. In particular, the thin film of oil covers the target insect or mite and plugs the spiracles or pores through which such pests or parasites breathe. Thus the cause of death may be suffocation. The non-toxic aqueous pesticide may also breakdown or dissolve the exoskeleton of the parasites. Large, motile insects and animals that breathe by another method are not affected by these oils. Further, since the high terpene containing oils are natural oils, the non-toxic aqueous pesticide is environmentally acceptable and has little, if any deleterious effect on wildlife and non-target insects.

Surfactants such as anionic and nonionic surfactants are acceptable for use in the non-toxic aqueous pesticide of the present invention. Preferred are anionic surfactants such as salts of fatty acids, alkyl sulphates, alkyl ether sulphonates and alkyl aryl sulphonates. Examples of preferred surfactants include about 10 per cent sulfonic acid, about 6 per cent to about 7 per cent sodium laurel sulfate, from about 8 per cent to about 12 per cent alcohol ethoxylate and from about 1 per cent to about 2 per cent olefin sulfonate.

Generally, the non-toxic aqueous pesticide will contain from about 10 per cent to about 40 per cent by weight of surfactant(s), preferably from about 20 per cent to about 35 per cent by weight and more preferably from about 25 per cent to about 30 per cent by weight.

The non-toxic aqueous pesticide may also contain various additives such as preservatives, pH neutralizers and/or clarifiers or stabilizers.

Such preservatives may include butylated hydroxytoluene (BHT), p-Hydroxybenzoic acid, fungicide and bactericide.

The butylated hydroxytoluene (BHT) acts as an antioxidant. The antioxidant range from about 0.008 per cent to about 0.02 per cent by weight and more preferably about 0.01 per cent by weight.

The fungicide such as Borax (10 mole) is from about 0.1 per cent to about 5 per cent by weight, preferably from about 0.5 per cent to about 2.0 per cent by weight and more preferably about 1.0 per cent by weight.

The p-Hydroxybenzoic acid is from about 0.4 per cent to about 0.8 per cent by weight and more preferable about 0.6 per cent.

The bactericide is from about 0.3 per cent to about 0.5 per cent, preferably about 0.4 per cent solution.

Caustic crystals such as sodium hydroxide may be added in an amount from about 1.0 per cent to about 1.5 per cent by weight to neutralize the composition and more preferably about 1.3 per cent by weight.

An example of a suitable clarifier or stabilizer is urea in an amount from about 0.5 per cent to about 1.5 per cent by weight and more preferably about 0.9 per cent by weight.

Since the non-toxic aqueous pesticide is an aqueous composition, the balance of the non-toxic aqueous pesticide is from about 60 per cent to about 70 per cent of water by weight.

The preferred non-toxic aqueous pesticide comprises about 6 per cent cold pressed orange oil, about 6.9 per cent sodium lauryl sulfate, about 11.6 per cent of alcohol ethoxylate, about 1.7 per cent sodium olefin sulfonate, about 10.2 per cent sulphonic acid, about 0.01 per cent butylate hydroxytoluene, about 0.58 per cent p-Hydroxybenzoic acid, about 0.4 per cent bactericide, about 1.0 per cent fungicide, about 0.9 per cent urea and about 1.3 per cent sodium hydroxide caustic crystal with the balance a diluent such as water, all by weight.

In use, the non-toxic aqueous pesticide is diluted with water and sprayed or misted on the host whether plant or animal to directly contact the surface of the target pests. An effective dilution rate of from about 1:10 to about 1:600 by weight. In some cases, repeated applications may be required.

When so applied, the non-toxic aqueous pesticide has been effective in controlling darkling beetles, lice, ticks, mites, flies, aphides, mosquitoes and chiggers. Since the mechanism of insect and mite control with spray oils is by suffocation and/or breakdown the waxy layer on the exoskeleton, there is no requirement for the addition of toxic chemicals. As such, the instant invention provides a virtually non-toxic alternative as applied to broad-spectrum insecticides.

The non-toxic aqueous pesticide is preferably applied as a mist or fog at from about 2 per cent to about 6 per cent solution, but the most preferred solution for application on animals is about 4 per cent.

The method of producing the non-toxic aqueous pesticide on plants and animals comprising the steps of adding the following constituents into a vessel: about 55 per cent diluent such as water; about 10.2 per cent such as sulfonic acid; about 1.32 per cent neutralizer such as NaOH (pellets); about 0.86 per cent stabilizer such as urea; about 6.87 per cent surfactant such as sodium laurel sulfate; about 8.59 per cent surfactant such as alcohol ethoxylate and about 1.71 per cent surfactant such as olefin sulfonate.

Dissolving 0.01 per cent antioxidant such as butylated hydroxytoluene (BHT) in about 5.78 per cent essential oil such as orange oil and adding combination to the vessel. Adding about 0.58 per cent preservative such as p-Hydroxybenzoic acid. Dissolving about 0.99 per cent preservative (fungicide) such as fungicide and about 0.40 per cent preservative (bactericide) in water and adding combination to the vessel. Adding about 7.50 per cent diluent such as water and mix for 30 minutes or until solids are dissolved.

Adjusting the pH from about 7.75 to about 9 by adding an effective amount of NaOH or Citric Acid granules and finally adjusting the viscosity by adding about 3 per cent alcohol ethoxylate.

While the invention has been described above with respect to certain particular embodiments thereof, numerous other forms and modifications will be apparent to those skilled in the art. The appended claims and the invention generally should be construed as covering all such obvious forms and modifications which are within the true spirit and scope of the invention.

What is claimed is:

1. A method of controlling insects and parasites found on plants and animals by applying a nontoxic aqueous pesticide to the plant or animal, said pesticide comprising at least one surfactant selected from the group consisting of sodium laurel sulphate, alcohol ethoxylate, olefin sulphonate, sulphonic acid and mixtures thereof and at least one high terpene containing natural oil selected from the group consisting of citrus peel oils, pine oils and mixtures thereof, the pesticide containing from about 20% to about 35% of said at least one surfactant by weight percent and from about 4% to about 10% of said at least one high terpene containing natural oil by weight percent and from about 60% to about 70% of water by weight percent, said pesticide diluted with water at a dilution rate of from about 2% to about 6% by weight percent of said pesticide for application to the plant or animal to effectively control the insects and parasites.

2. The method of claim 1 containing from about 25 % to about 30% of said surfactants by weight percent and from about 5% to about 7% of said high terpene containing natural oils by weight percent.

3. The method of claim 1 further containing from about 0.30% to about 0.5% bactericide by weight percent.

4. A method of controlling insects and parasites found on plants and animals by applying a nontoxic aqueous pesticide to the plant or animal, said pesticide comprising from about 5% to about 7% orange oil by weight percent, from about 6% to about 7% sodium laurel sulphate by weight percent, from about 8% to about 12% alcohol ethoxylate by weight percent, from about 1% to about 2% olefin sulfonate by weight percent and about 10% sulphonic acid by weight percent and about 60% to about 70% of water by weight percent, said pesticide diluted with water at a dilution rate of from about 2% to about 6% by weight percent of said pesticide for application to the plant or animal to effectively control the insects and parasites.

5. The method of claim 4 further containing from about 0.008% to about 0.02% butylated hydroxytoluene by weight percent, from about 0.5% to about 2.0% fungicide by weight percent, from about 0.5% to about 1.5% urea by weight percent and from about 1.0% to about 1.5% sodium hydroxide by weight percent.

6. The method of claim 4 further containing from about 0.3% to about 0.5% bactericide by weight percent.

7. A method of controlling insects and parasites found on plants and animals by applying a nontoxic aqueous pesticide to the plant or animal, said pesticide comprising about 6% orange oil by weight percent, about 7% sodium laurel sulphate by weight percent, about 11.6% alcohol ethoxylate by weight percent, about 1.7% olefin sulfonate by weight percent and about 10.2% sulphonic acid by weight percent and about 60% to about 70% of water by weight percent, said pesticide diluted with water at a dilution rate of from about 4% by weight percent of said pesticide for application to the plant or animal to effectively control the insects and parasites.

8. The method of claim 7 further containing about 0.01% butylated hydroxytoluene by weight percent, about 1.0% fungicide by weight percent, about 0.9% urea by weight percent and about 1.3% sodium hydroxide by weight percent.

9. The method of claim 7 further containing about 0.4% bactericide by weight percent.

* * * * *